(12) United States Patent
Huizenga et al.

(10) Patent No.: US 8,755,915 B2
(45) Date of Patent: Jun. 17, 2014

(54) SENSOR INTERFACE FOR WIRELESS CONTROL

(75) Inventors: Charles Huizenga, Berkeley, CA (US); Michael G. Corr, San Francisco, CA (US); John Douglas Paton, Piedmont, CA (US)

(73) Assignee: ABL IP Holding LLC, Atlanta, GA (US)

(*) Notice: Subject to any disclaimer, the term of this patent is extended or adjusted under 35 U.S.C. 154(b) by 0 days.

(21) Appl. No.: 13/590,981

(22) Filed: Aug. 21, 2012

(65) Prior Publication Data

US 2012/0330476 A1 Dec. 27, 2012

Related U.S. Application Data

(63) Continuation of application No. 12/912,717, filed on Oct. 26, 2010, now Pat. No. 8,275,471.

(60) Provisional application No. 61/258,845, filed on Nov. 6, 2009, provisional application No. 61/258,841, filed on Nov. 6, 2009.

(51) Int. Cl.
*G05B 11/01* (2006.01)
*G05B 15/00* (2006.01)

(52) U.S. Cl.
USPC ............. 700/22; 700/17; 700/19; 700/83

(58) Field of Classification Search
USPC ............. 700/17, 19–20, 22, 65, 83; 307/38
See application file for complete search history.

(56) References Cited

U.S. PATENT DOCUMENTS

| 3,733,528 | A | 5/1973 | Gilbreath |
| 3,735,141 | A | 5/1973 | Beling |
| 4,242,614 | A | 12/1980 | Vatis et al. |
| 4,323,820 | A | 4/1982 | Teich |
| 4,347,461 | A | 8/1982 | Carlson |
| 4,355,309 | A | 10/1982 | Hughey et al. |
| 4,358,717 | A | 11/1982 | Elliott |
| 4,388,567 | A | 6/1983 | Yamazaki et al. |
| 4,454,509 | A | 6/1984 | Buennagel et al. |
| 4,686,380 | A | 8/1987 | Angott |
| 4,797,599 | A | 1/1989 | Ference et al. |
| 4,889,999 | A | 12/1989 | Rowen |
| 5,005,211 | A | 4/1991 | Yuhasz |
| 5,146,153 | A | 9/1992 | Luchaco et al. |
| 5,237,264 | A | 8/1993 | Moseley et al. |
| 5,248,919 | A | 9/1993 | Hanna et al. |
| 5,268,631 | A | 12/1993 | Gorman et al. |

(Continued)

OTHER PUBLICATIONS

Adams, J.T., "Wireless Sensors and Controls Make the Organic Building," May 2006, Proceedings of the 2006 IEEE Intl. Symposium on Electronics and the Environment, pp. 109-113.

(Continued)

*Primary Examiner* — Ramesh Patel
(74) *Attorney, Agent, or Firm* — Carr & Ferrell LLP

(57) ABSTRACT

Systems and methods for enabling communication with a wired sensor are provided. A wired sensor may be adapted for wireless communication using a sensor interface. A sensor interface is communicatively coupled with a wired sensor that provides information about a detected environmental condition. The sensor interface wirelessly transmits information received from the wired sensor to a controller that may control an electrical load based on the wirelessly transmitted information.

20 Claims, 6 Drawing Sheets

(56) References Cited

U.S. PATENT DOCUMENTS

| | | | |
|---|---|---|---|
| 5,357,170 A | 10/1994 | Luchaco et al. | |
| 5,373,453 A | 12/1994 | Bae | |
| 5,471,063 A | 11/1995 | Hayes et al. | |
| 5,561,351 A | 10/1996 | Vrionis et al. | |
| 5,572,438 A * | 11/1996 | Ehlers et al. | 700/295 |
| 5,637,930 A | 6/1997 | Rowen et al. | |
| 5,770,926 A | 6/1998 | Choi et al. | |
| 5,818,128 A | 10/1998 | Hoffman et al. | |
| 5,822,012 A * | 10/1998 | Jeon et al. | 348/553 |
| 5,872,429 A | 2/1999 | Xia et al. | |
| 5,905,442 A | 5/1999 | Mosebrook et al. | |
| 5,909,087 A | 6/1999 | Bryde et al. | |
| 5,927,603 A | 7/1999 | McNabb | |
| 5,962,989 A | 10/1999 | Baker | |
| 5,982,103 A | 11/1999 | Mosebrook et al. | |
| 6,025,783 A | 2/2000 | Steffens, Jr. | |
| 6,044,062 A | 3/2000 | Brownrigg et al. | |
| 6,100,653 A | 8/2000 | Lovell et al. | |
| 6,108,614 A | 8/2000 | Lincoln et al. | |
| 6,148,306 A | 11/2000 | Seidl et al. | |
| 6,169,377 B1 | 1/2001 | Bryde et al. | |
| 6,175,860 B1 * | 1/2001 | Gaucher | 709/208 |
| 6,184,622 B1 | 2/2001 | Lovell et al. | |
| 6,249,516 B1 | 6/2001 | Brownrigg et al. | |
| 6,252,358 B1 | 6/2001 | Xydis et al. | |
| 6,297,724 B1 | 10/2001 | Bryans et al. | |
| 6,300,727 B1 | 10/2001 | Bryde et al. | |
| 6,301,674 B1 | 10/2001 | Saito et al. | |
| 6,311,105 B1 | 10/2001 | Budike, Jr. | |
| 6,388,399 B1 | 5/2002 | Eckel et al. | |
| 6,400,280 B1 | 6/2002 | Osakabe | |
| 6,504,266 B1 | 1/2003 | Ervin | |
| 6,510,369 B1 | 1/2003 | Lacy | |
| 6,535,859 B1 | 3/2003 | Yablonowski et al. | |
| 6,548,967 B1 * | 4/2003 | Dowling et al. | 315/318 |
| 6,633,823 B2 | 10/2003 | Bartone et al. | |
| 6,640,142 B1 | 10/2003 | Wong et al. | |
| 6,689,050 B1 | 2/2004 | Beutter et al. | |
| 6,700,334 B2 | 3/2004 | Weng | |
| 6,803,728 B2 | 10/2004 | Balasubramaniam et al. | |
| 6,891,838 B1 | 5/2005 | Petite et al. | |
| 6,904,385 B1 | 6/2005 | Budike, Jr. | |
| 6,914,395 B2 | 7/2005 | Yamauchi et al. | |
| 6,914,893 B2 | 7/2005 | Petite | |
| 6,927,546 B2 | 8/2005 | Adamson et al. | |
| 6,990,394 B2 * | 1/2006 | Pasternak | 700/295 |
| 7,006,768 B1 | 2/2006 | Franklin | |
| 7,039,532 B2 | 5/2006 | Hunter | |
| 7,042,170 B2 | 5/2006 | Vakil et al. | |
| 7,045,968 B1 | 5/2006 | Bierman et al. | |
| 7,054,271 B2 | 5/2006 | Brownrigg et al. | |
| 7,079,808 B2 | 7/2006 | Striemer | |
| 7,103,511 B2 | 9/2006 | Petite | |
| 7,167,777 B2 | 1/2007 | Budike, Jr. | |
| 7,199,530 B2 | 4/2007 | Vakil et al. | |
| 7,233,080 B2 | 6/2007 | Garnault et al. | |
| 7,263,073 B2 | 8/2007 | Petite et al. | |
| 7,274,975 B2 | 9/2007 | Miller | |
| 7,307,389 B2 | 12/2007 | Vakil et al. | |
| 7,307,542 B1 | 12/2007 | Chandler et al. | |
| 7,333,880 B2 | 2/2008 | Brewster et al. | |
| 7,339,466 B2 * | 3/2008 | Mansfield et al. | 340/538 |
| 7,346,433 B2 | 3/2008 | Budike, Jr. | |
| 7,349,766 B2 | 3/2008 | Rodgers | |
| 7,352,972 B2 | 4/2008 | Franklin | |
| 7,354,175 B2 | 4/2008 | Culbert et al. | |
| 7,356,308 B2 | 4/2008 | Hamada et al. | |
| 7,369,060 B2 | 5/2008 | Veskovic et al. | |
| 7,400,226 B2 | 7/2008 | Barrieau et al. | |
| 7,417,556 B2 | 8/2008 | Ling | |
| 7,432,803 B2 | 10/2008 | Fails et al. | |
| 7,446,671 B2 | 11/2008 | Giannopoulos et al. | |
| 7,490,957 B2 | 2/2009 | Leong et al. | |
| 7,491,111 B2 | 2/2009 | Ghaly | |
| 7,528,503 B2 | 5/2009 | Rognli et al. | |
| 7,561,977 B2 | 7/2009 | Horst et al. | |
| 7,565,227 B2 | 7/2009 | Richard et al. | |
| 7,571,063 B2 | 8/2009 | Howell et al. | |
| 7,599,764 B2 | 10/2009 | Matsuura et al. | |
| 7,606,639 B2 | 10/2009 | Miyaji | |
| 7,623,042 B2 * | 11/2009 | Huizenga | 340/641 |
| 7,650,425 B2 | 1/2010 | Davis et al. | |
| 7,659,674 B2 | 2/2010 | Mueller et al. | |
| 7,677,753 B1 | 3/2010 | Wills | |
| 7,697,927 B1 | 4/2010 | Owens | |
| 7,706,928 B1 | 4/2010 | Howell et al. | |
| 7,719,440 B2 | 5/2010 | Delp et al. | |
| 7,755,505 B2 | 7/2010 | Johnson et al. | |
| 7,760,068 B2 | 7/2010 | Hatemata et al. | |
| 7,783,188 B2 | 8/2010 | Clark | |
| 7,812,543 B2 | 10/2010 | Budike, Jr. | |
| 7,839,017 B2 * | 11/2010 | Huizenga et al. | 307/38 |
| 7,843,353 B2 | 11/2010 | Pan et al. | |
| 7,860,495 B2 * | 12/2010 | McFarland | 455/420 |
| 7,880,394 B2 | 2/2011 | Sibalich et al. | |
| 7,884,732 B2 * | 2/2011 | Huizenga | 340/635 |
| 7,889,051 B1 | 2/2011 | Billig et al. | |
| 7,902,759 B2 | 3/2011 | Newman, Jr. | |
| 7,925,384 B2 * | 4/2011 | Huizenga et al. | 700/277 |
| 8,275,471 B2 * | 9/2012 | Huizenga et al. | 700/22 |
| 8,364,325 B2 * | 1/2013 | Huizenga et al. | 700/295 |
| 2001/0015409 A1 | 8/2001 | Mahler et al. | |
| 2001/0025349 A1 * | 9/2001 | Sharood et al. | 713/340 |
| 2002/0009978 A1 | 1/2002 | Dukach et al. | |
| 2002/0043938 A1 | 4/2002 | Lys | |
| 2003/0020595 A1 | 1/2003 | Wacyk | |
| 2003/0209999 A1 | 11/2003 | Hui et al. | |
| 2004/0002792 A1 | 1/2004 | Hoffknecht | |
| 2004/0051467 A1 | 3/2004 | Balasubramaniam et al. | |
| 2004/0100394 A1 | 5/2004 | Hitt | |
| 2005/0043862 A1 | 2/2005 | Brickfield et al. | |
| 2005/0090915 A1 | 4/2005 | Geiwitz | |
| 2005/0234600 A1 | 10/2005 | Boucher et al. | |
| 2006/0044152 A1 | 3/2006 | Wang | |
| 2006/0142900 A1 | 6/2006 | Rothman et al. | |
| 2006/0215345 A1 | 9/2006 | Huizenga | |
| 2006/0244624 A1 | 11/2006 | Wang et al. | |
| 2006/0291136 A1 | 12/2006 | Okishima | |
| 2007/0005195 A1 | 1/2007 | Pasquale et al. | |
| 2007/0085700 A1 | 4/2007 | Walters et al. | |
| 2007/0090960 A1 | 4/2007 | Miki | |
| 2007/0229250 A1 | 10/2007 | Recker et al. | |
| 2007/0271006 A1 | 11/2007 | Golden et al. | |
| 2007/0273307 A1 | 11/2007 | Westrick et al. | |
| 2007/0276547 A1 | 11/2007 | Miller | |
| 2008/0071391 A1 | 3/2008 | Busby et al. | |
| 2008/0133065 A1 | 6/2008 | Cannon et al. | |
| 2008/0167756 A1 | 7/2008 | Golden et al. | |
| 2008/0242314 A1 | 10/2008 | McFarland | |
| 2008/0258633 A1 * | 10/2008 | Voysey | 315/159 |
| 2008/0281473 A1 | 11/2008 | Pitt | |
| 2009/0018706 A1 | 1/2009 | Wittner | |
| 2009/0026966 A1 | 1/2009 | Budde et al. | |
| 2009/0045941 A1 | 2/2009 | Cooper | |
| 2009/0048691 A1 | 2/2009 | Donaldson | |
| 2009/0055032 A1 | 2/2009 | Rodgers | |
| 2009/0058193 A1 | 3/2009 | Reid et al. | |
| 2009/0063257 A1 | 3/2009 | Zak et al. | |
| 2009/0066473 A1 | 3/2009 | Simons | |
| 2009/0072945 A1 | 3/2009 | Pan et al. | |
| 2009/0132070 A1 | 5/2009 | Ebrom et al. | |
| 2009/0198384 A1 | 8/2009 | Ahn | |
| 2009/0218951 A1 | 9/2009 | Weaver | |
| 2009/0240381 A1 | 9/2009 | Lane | |
| 2009/0243517 A1 | 10/2009 | Verfuerth et al. | |
| 2009/0248217 A1 | 10/2009 | Verfuerth et al. | |
| 2009/0261735 A1 | 10/2009 | Sibalich et al. | |
| 2009/0262189 A1 | 10/2009 | Marman | |
| 2009/0267540 A1 * | 10/2009 | Chemel et al. | 315/297 |
| 2009/0278472 A1 | 11/2009 | Mills et al. | |
| 2009/0292402 A1 | 11/2009 | Cruickshank, III | |
| 2009/0292403 A1 | 11/2009 | Howell et al. | |
| 2009/0299527 A1 | 12/2009 | Huizenga et al. | |
| 2010/0039240 A1 | 2/2010 | Rodriguez et al. | |

(56) References Cited

U.S. PATENT DOCUMENTS

| | | | |
|---|---|---|---|
| 2010/0052939 | A1 | 3/2010 | Liang |
| 2010/0066267 | A1 | 3/2010 | Meyer |
| 2010/0114340 | A1 | 5/2010 | Huizenga et al. |
| 2010/0134019 | A1 | 6/2010 | Berhorst |
| 2010/0134051 | A1 | 6/2010 | Huizenga et al. |
| 2010/0141153 | A1* | 6/2010 | Recker et al. ............ 315/149 |
| 2010/0164386 | A1 | 7/2010 | You |
| 2010/0179670 | A1* | 7/2010 | Forbes et al. ............ 700/22 |
| 2010/0185339 | A1 | 7/2010 | Huizenga et al. |
| 2010/0191388 | A1 | 7/2010 | Huizenga |
| 2010/0201203 | A1 | 8/2010 | Schatz et al. |
| 2010/0204847 | A1* | 8/2010 | Leete et al. ............ 700/295 |
| 2010/0207548 | A1 | 8/2010 | Iott |
| 2010/0237783 | A1 | 9/2010 | Dupre et al. |
| 2010/0265100 | A1 | 10/2010 | Jalbout et al. |
| 2011/0006877 | A1 | 1/2011 | Franklin |
| 2011/0012541 | A1 | 1/2011 | Finch |
| 2011/0043052 | A1 | 2/2011 | Huizenga et al. |
| 2011/0101871 | A1 | 5/2011 | Schenk et al. |
| 2011/0109424 | A1 | 5/2011 | Huizenga et al. |
| 2011/0112702 | A1 | 5/2011 | Huizenga et al. |

OTHER PUBLICATIONS

Canovas, S. R., Chermont, M.G., and Cugnasaca, C.E., "Remote Monitoring and Actuation Based on LonWorks Technology," Jul. 2005, 2005 EFITA/WCCA Joint Congress on IT in Agriculture.

Gislason, D. and Gillman, T. "ZigBee Wireless Sensor Networks," Nov. 2004, Dr. Dobbs online journal, www.ddj.com/184405887.

Gutierrez, J.A., "On the Use of IEEE Std. 802, 15.4 to enable Wireless Sensor Networks in Building Automation," Dec. 2007, Int'l. Journal of Wireless Information Network, vol. 14, No. 4.

Kintner-Meyer, M. "Opportunities of Wireless Sensors and Controls for Building Operations," Aug.-Sep. 2005, Energy Engineering, vol. 102, No. 5, pp. 27-48.

Motegi, N., Piette, M., Kinney, S., and Herter, K., "Web-Based Energy Information Systems for Energy Management and Demand Response in Commercial Buildings," Apr. 2003, Lawrence Berkeley National Laboratory.

Park, H., Burke, J., and Srivastava, M., "Design and Implementation of a Wireless Sensor Network for Intelligent Light Control," Apr. 2007, IPSN 07.

Sandhu, J.S.S., Agogino, A.M., "Wireless Sensor Networks for Commercial Lighting Control: Decision Making with Multi-Agent Systems," Jul. 2004, Workshop on Sensor Networks.

Sandhu, J.S., Agogino, A.M., and Agogino, A.K., "Wireless Sensor Networks for Commercial Lighting Control: Decision Making with Multi-Agent Systems," 2004, American Assocation for Artificial Intelligence.

Sekinger, J., "Wireless Lighting Control Technology," Oct. 2005, Phillips NAESCO Midwest Regional Mtgs.

Singhvi, V., Krause, A., Guestrin, C., Garrett, J.H., Matthews, H.S. "Intelligent Light Control Usine Sensor Networks," Nov. 2005, SenSys 2005.

Teasdale, D., Rubinstein, F., Watson, D., and Purdy, S., "Annual Technical Progress Report: Adapting Wireless Technology to Lighting Control and Environmental Sensing," Oct. 2005, Dust Networks, Annual Technical Progress Report.

Wang, D., Arens, E., and Federspiel, C., "Opportunities to Same Energy and Improve Comfort by Using Wireless Sensor Networks in Buildings," Oct. 2003, Proceedings of the third intl Conference for Enhanced Building Operations.

Non-Final Office Action, May 7, 2008, U.S. Appl. No. 11/376,620, filed Mar. 14, 2006.
Final Office Action, Oct. 17, 2008, U.S. Appl. No. 11/376,620, filed Mar. 14, 2006.
Non-Final Office Action, Mar. 5, 2009, U.S. Appl. No. 11/376,620, filed Mar. 14, 2006.
Notice of Allowance, Oct. 5, 2009, U.S. Appl. No. 11/376,620, filed Mar. 14, 2006.
Notice of Allowance, Oct. 20, 2009, U.S. Appl. No. 11/376,620, filed Mar. 14, 2006.
Non-Final Office Action, Apr. 16, 2012, U.S. Appl. No. 12/156,621, filed Jun. 2, 2008.
Final Office Action, Sep. 10, 2010, U.S. Appl. No. 12/156,621, filed Jun. 2, 2008.
Non-Final Office Action, Apr. 13, 2011, U.S. Appl. No. 12/156,621, filed Jun. 2, 2008.
Final Office Action, Dec. 7, 2011, U.S. Appl. No. 12/156,621, filed Jun. 2, 2008.
Notice of Allowance, Aug. 20, 2012, U.S. Appl. No. 12/156,621, filed Jun. 2, 2008.
Non-Final Office Action, Oct. 14, 2011, U.S. Appl. No. 12/912,717, filed Oct. 26, 2010.
Notice of Allowance, May 21, 2012, U.S. Appl. No. 12/912,717, filed Oct. 26, 2010.
Non-Final Office Action, May 26, 2011, U.S. Appl. No. 12/940,902, filed Nov. 5, 2010.
Final Office Action, Feb. 23, 2012, U.S. Appl. No. 12/940,902, filed Nov. 5, 2010.
Non-Final Office Action, Oct. 10, 2012, U.S. Appl. No. 12/940,902, filed Nov. 5, 2010.
Final Office Action, Apr. 26, 2013, U.S. Appl. No. 12/940,902, filed Nov. 5, 2010.
Advisory Action, Jul. 9, 2013, U.S. Appl. No. 12/940,902, filed Nov. 5, 2010.
Non-Final Office Action, Apr. 19, 2010, U.S. Appl. No. 12/613,970, filed Nov. 6, 2009.
Final Office Action, Jul. 23, 2010, U.S. Appl. No. 12/613,970, filed Nov. 6, 2009.
Non-Final Office Action, Oct. 5, 2011, U.S. Appl. No. 12/613,970, filed Nov. 6, 2009.
Final Office Action, Jun. 28, 2012, U.S. Appl. No. 12/613,970, filed Nov. 6, 2009.
Non-Final Office Action, Jul. 6, 2010, U.S. Appl. No. 12/380,727, filed Mar. 2, 2009.
Notice of Allowance, Sep. 8, 2010, U.S. Appl. No. 12/380,727, filed Mar. 2, 2009.
Non-Final Office Action, Jul. 8, 2010, U.S. Appl. No. 12/579,353, filed Oct. 14, 2009.
Notice of Allowance, Oct. 28, 2010, U.S. Appl. No. 12/579,353, filed Oct. 14, 2009.
Notice of Allowance, Dec. 20, 2010, U.S. Appl. No. 12/579,353, filed Oct. 14, 2009.
Non-Final Office Action, Jun. 6, 2010, U.S. Appl. No. 12/690,875, filed Jan. 20, 2010.
Notice of Allowance, Dec. 10, 2010, U.S. Appl. No. 12/690,875, filed Jan. 20, 2010.
Notice of Allowance, Mar. 4, 2011, U.S. Appl. No. 12/690,875, filed Jan. 20, 2010.
Non-Final Office Action, Feb. 2, 2012, U.S. Appl. No. 12/913,725, filed Oct. 27, 2010.

* cited by examiner

SENSOR INTERFACE FOR WIRELESS CONTROL

CROSS-REFERENCE TO RELATED APPLICATION

This application is a continuation of application Ser. No. 12/912,717, filed on Oct. 26, 2010 now U.S. Pat. No. 8,275,471, which claims the priority benefit of U.S. provisional application No. 61/258,845 filed Nov. 6, 2009 and U.S. provisional application No. 61/258,841 filed Nov. 6, 2009. All of the above disclosures are incorporated herein by reference.

This application is also related to U.S. patent application Ser. No. 12/156,621 filed Jun. 2, 2008 and U.S. patent application Ser. No. 12/380,727 filed Mar. 2, 2009, the disclosures of which are also incorporated herein by reference.

BACKGROUND OF THE INVENTION

1. Field of the Invention

The present invention generally involves wireless control. More specifically, the present invention relates to a sensor interface for enabling wireless communication with a wired sensor.

2. Description of Related Art

In recent years, a growing concern over environmental responsibility and viability has prompted various measures to reduce energy consumption and ensuing costs. In commercial and residential settings, one solution is the use of a sensor for detecting certain environmental conditions and initiating a adjustment of an electrical load device (i.e., electricity-consuming device) in response to the detected condition(s). For example, some building installations (e.g., offices) have installed occupancy sensors to detect motion in a given location. An occupancy sensor wired to a lighting fixture, for example, may detect movement or lack of movement in a particular room and cause the lighting fixture to turn on or off in response. Such sensor may initiate such response by communicating with an actuator or switch of the electrical load device.

Issues with such a scheme may include inflexibility and difficulty and expense associated with retrofitting for changing and/or growing installations. For example, a sensor may have to be rewired when electrical load devices are added, removed, or relocated and when user preferences change. Such situations may require rewiring and reconfiguration of sensor settings to reflect the new arrangement and requirements thereof. While wireless control solutions may allow for increased flexibility, implementing wireless solutions may include installing new wireless sensors, which may be costly for some installations.

There is therefore a need in the art for enabling wireless communications with wired sensors.

SUMMARY OF THE INVENTION

Embodiments of the present invention provide systems and methods for enabling wireless communication with a wired sensor. Power is supplied continuously to an electrical load device under control of a wireless controller. A wired sensor detects an environmental condition. The detected information may be received at a wireless interface communicatively coupled to the wired sensor. The wireless interface transmits the detected information to the wireless controller, which may then control operation of the electrical load device based on the detected information.

Further embodiments of the present invention may include systems for enabling wireless communication with wired sensors. Such systems may include a power source for supplying continuous power to an electrical load device that operates under control of a wireless controller and a sensor interface communicatively coupled to the wired sensor. Such a sensor interface may receive information regarding an environmental condition detected by the wired sensor and wirelessly transmit the information to the wireless controller. The wireless controller may then control operation of the electrical load device based on the information wirelessly transmitted from the sensor interface.

Embodiments of the present invention may further include methods for enabling wireless communication with a wired sensor. Such methods ma include monitoring a wired sensor for generation of a signal indicating detection of an environmental condition, receiving a signal from the wired sensor at a sensor interface, regarding the environmental condition detected by the wired sensor, and wirelessly transmitting the information regarding the environmental condition from the sensor interface to a wireless controller. The wireless controller may then control operation of an electrical load device based on the information wirelessly transmitted from the sensor interface.

Further embodiments may include apparatuses for enabling wireless communication with a wired sensor and computer-readable storage media for performing methods for enabling wireless communication with a wired sensor.

DETAILED DESCRIPTION

The present invention provides systems and methods for enabling wireless communication with a wired sensor. These systems and methods may be used to retrofit building installations by adapting pre-existing, wired sensors for wireless communication with wireless control systems. A sensor interface may be communicatively coupled with a sensor that provides information about a detected environmental condition. The sensor interface may wirelessly transmit information received from the sensor to a controller that may control an electrical load device based on the wirelessly transmitted information. Controlling an electrical load device, for example, may allow a building owner or facility manager to adapt to changing conditions and optimize operation of electrical load devices (e.g., lighting, room temperature), thereby reducing waste and energy costs.

Figure 1:
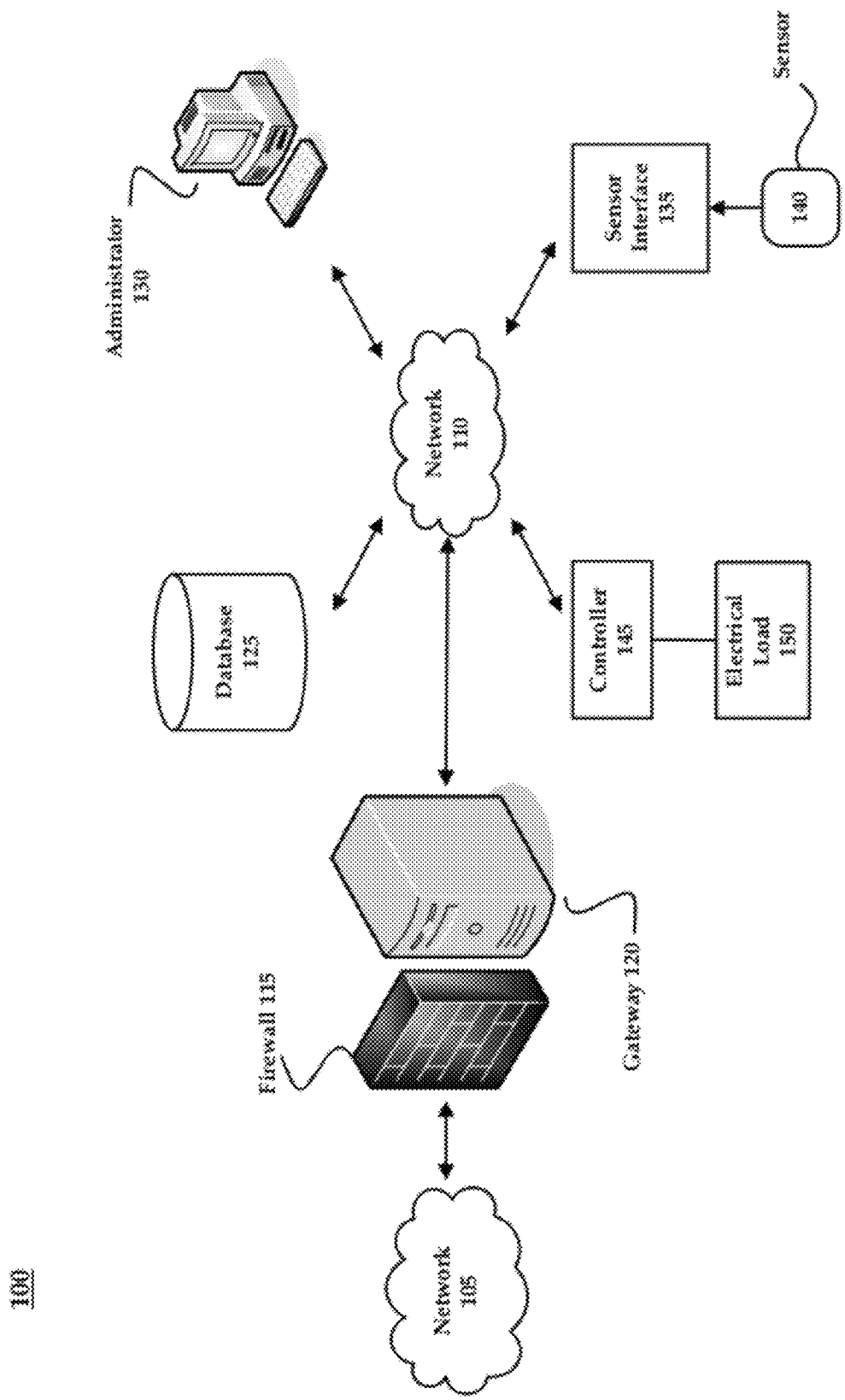
FIG. 1 is a network environment in which may be implemented an exemplary system for enabling wireless communication with a wired sensor.

FIG. 1 is a network environment 100 in which may be implemented an exemplary system for enabling wireless communication with a wired sensor. The network environment 100 of FIG. 1 includes communications network 105 and 110, firewall 115, gateway 120, database 125, administrator station 130, sensor interface 135, wired sensor 140, controller 145, and electrical load device 150. Although only a single controller and electrical load device are shown in FIG. 1, alternative embodiments may include multiple controllers each controlling one or more electrical load devices. The number of sensors, controllers, and electrical load devices may vary for different implementations. Network environment 100 may be implemented among various public or private, indoor or outdoor locations, such as office buildings, retail facilities, restaurants, warehouses, schools, campuses, parks, stadiums, or parking garages.

Communication networks 105 and 110 may include any of the various wireless communication networks that are known in the art, such as the Internet, Wide Area Network (WAN), Local Area Network (LAN), intranet, extranet, private network, or other network. As illustrated in FIG. 1, communication network 105 may be a WAN that may be communicatively coupled to a LAN. Communication networks 105 and 110 allow for communication between the various parties in network environment 100. In one embodiment, communication networks 105 and 110 may include a multi-hop, wireless mesh network.

Network environment 100, also referred to as wireless control system 100, may include a firewall 115 and wireless gateway 120 as are known in the art, for ensuring secure data transmission and network. Database 125 may be any database known in the art for storing and managing data concerning wireless control system 100. Database 125 may be housed separately or in association with administrator station 130, sensor interface 135, or controller 145. Database 125 may store, among other things, data or information received from sensor 140. Database 125 may also include other historical and operational data concerning device status, occupancy information, operating schedules, lighting levels, lighting parameters, other conditions and parameters, operating instructions, automated responses to signals from certain parties (e.g., demand response), preferences, energy usage, equipment failures, etc. Such data as stored in database 125 may be factored into control decisions by controller 145 with respect to directing operation of electrical load device 150.

Administrator station 130 is inclusive of a general purpose computing device such as that illustrated in FIG. 6, described in detail below. Administrator station 130 may be implemented as a computing device such as a workstation, server, desktop computer, laptop computer, mobile device, or other computing device. Administrator station 130 may be used to receive and manage administrator settings regarding schedules, monitoring parameters, and/or control over the various components of the network environment 100. For example, instead of manually programming various thresholds for each sensor 140, such preferred operational settings may take multiple factors into consideration (e.g., amount of detected motion correlated to time delay, amount of detected daylight correlated to hours of operation) may be inputted at administrator station 130 and implemented via sensor interface 135 and/or controller 145.

Administrator station 130 may also be used to control one or more electrical load devices 150 via controller 145. A facilities manager or other user, for example, may use administrator station 130 to manually control or input relevant parameters that may be factored into control decisions in wireless control system 100. For example, the facilities manager or other user may use administrator station 130 to set preferences about operation of a particular electrical load device 150 under specified conditions. For example, administrator station 130 may provide a schedule of specific dates and/or times when a particular electrical load device 150 should be on or off or dimmed. Administrator station 130 may also perform other activities associated with wireless control system 100, including monitoring or tracking energy usage, predicting electrical load device failures (e.g., failure of a lamp or ballast), managing demand response events, or responding to maintenance requirements.

Sensor 140 may be any wired sensor known in the art for detecting an environmental condition including but not limited to movement, light, temperature, or sound. Sensor 140 may be, for example, a motion detection sensor, occupancy sensor, optical sensor (e.g., infrared, laser), light sensor, image sensor, photo sensor, sound sensor, etc. In one embodiment, sensor 140 is a low voltage occupancy sensor (e.g., ultrasonic, passive infrared, dual technology). Sensor 140 may generate a signal upon detection of an environmental condition within an area surrounding the sensor 140. Information regarding environmental conditions detected by sensor 140 may be sent to database 125 for storage.

Sensor 140 is wired directly to the electrical load device 150 in all but the very newest buildings. Such sensors 140, and wiring thereof, may have been grandfathered in from the original construction or installation. Because changing the configuration or adjustment of such sensors 140 may require extensive retrofitting, rewiring, etc., changes and adjustments may have been difficult and consequently, rare. Associating the sensor 140 with a sensor interface 135 capable of wireless communication, however, allows for easy, on-the-fly adjustments. For example, a user who wishes to adjust a sensor threshold to be more or less sensitive does not have to physically reconfigure or rewire the sensor 140, but may simply send instructions over the wireless communication network 110 to the sensor interface 135. Any type of sensor 140 may therefore be associated with a sensor interface 135. Upon detection of a particular environmental condition, sensor 140 may send an indication to sensor interface 135, which may, in turn, wirelessly transmit that information to another device (e.g., controller 145) for further processing.

Communications sent from sensor 140 to sensor interface 135 may include digital signals (i.e., occupied vs. unoccupied), DC voltage, current, etc. Upon installation and/or connection to the sensor 140, the sensor interface 135 may determine the type of sensor based on information provided by sensor 140 (i.e., voltage pattern, range of voltage). For example, occupancy sensors are associated with a stepped voltage pattern, as an occupancy sensor only detects presence or lack of presence. In contrast, a light sensor may detect varying levels of light. Alternatively, the type of sensor and other sensor information may be provided to sensor interface 135 via programming and/or wirelessly transmitted updates.

Sensor 140 may be limited in the amount and type of information it can detect and/or transmit. For example, a sensor 140 may be a motion sensor that can only indicate whether motion is detected or not. There is no ability by the sensor 140 to provide any additional information, such as how much movement, the duration of the movement, and so on. In such circumstances, sensor interface 135 may be able to evaluate the information from sensor 140, as well as from other sources, to identify certain conditions with more detail. Referring to the previous example, the sensor interface 135 may track and evaluate the indications of movement sent by sensor 140. Receipt of multiple indications of movement in a predetermined amount of time, for example, may confirm presence of people in a room, rather than movement of passers-by outside a window or door of that room.

The ability to evaluate information sent by sensor 140 further means that sensor interface 135 may consider more factors in making actuation decisions. For example, sensor 140 may have been previously wired to actuate an electrical load device 150 (e.g., lamp) whenever movement is detected. Such wiring may result in wasted energy from actuation of the lamp 150 in response to detected movement that is unrelated to the presence of people in the room. Passing movement outside a window, for instance, may be detected by a sensor 140 inside the room and resulted in actuation of lamp 150, in spite of the fact that such movement does not indicate any need for light.

Sensor interface 135, on the other hand, may be programmed to require detection of movement over a predetermined period of time (e.g., several seconds) before actuating the electrical load device 150. Further, the predetermined period of time and other parameters may be adjusted based on instruction sent wirelessly from the administrator station 130 to the sensor interface 135. Additionally, one or more thresholds may be adjusted based on, for example, day of the week, time of day, holiday schedules, etc. For example, the predetermined period of time may be adjusted based on schedules, so that more movement is required to actuate lamp 150 on weekends and holidays than on weekdays. Sensor interfaces 135 may receive communications sent over the wireless communication network 110 regarding updates for thresholds and other parameters. In some embodiments, sensor interface 135 may operate in conjunction with controller 145 to intelligently respond to the conditions detected by sensor 140.

Controller 145 directly controls operation of an electrical load device 150 based on, among other things, information detected by sensor 140 and communicated via sensor interface 135 and wireless communication network 110. Controller 145 may encompass such control devices such as those described in U.S. patent application Ser. No. 12/156,621, the disclosure of which is incorporated by reference herein. Controller 145 may include a microcontroller or microprocessor-based computing platform designed to direct performance of various tasks. Rule-based or algorithmic actuation logic executed by the microcontroller may make control decisions to actuate the electrical load device 150 based on various factors, including the information provided by sensor 140 via sensor interface 135.

Controller 145 may also include a clock or schedule for internally tracking date and time and performing time-based operations. Controller 145 may also locally store information concerning schedule information, holiday information, and desired operating states in various conditions. Controller 145 may also provide information (e.g., to administrator station 130) regarding equipment determined or detected as having failed.

Electrical load device 150 illustrated in FIG. 1 may include any electricity-consuming device. For example, electrical load device 150 may be a device in a facility system for lighting (e.g., individual or cluster of lighting fixtures), heating, ventilating, air-conditioning (HVAC), fans, blinds, louvers, security systems, fire and life safety systems, irrigation systems, etc.

Figure 2:
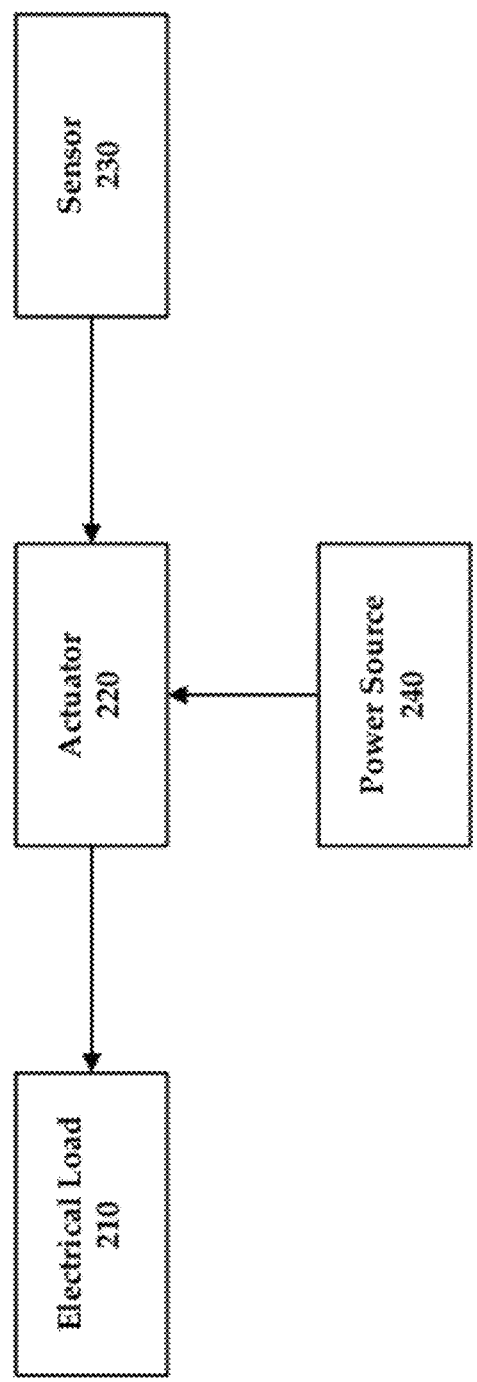
FIG. 2 is a diagram of a sensor system as known in the prior art.

FIG. 2 is a diagram of a sensor system 200 as known in the prior art. The prior art sensor system 200 of FIG. 2 includes electrical load device 210, actuator 220, sensor 230, and power source 240. Sensor 230 may communicate with actuator 220 (e.g., power pack or relay) which may control electrical load based on information received from sensor 230.

Generally speaking, actuator 220 may be any electrical component that can interrupt an electrical circuit or vary the power transferred via the electrical circuit. Actuator 220 may include any of a number of manually operated electromechanical devices, including a toggle switch, a rocker switch, a push-button switch, and a momentary contact switch. Actuator 220 may have one or more sets of electrical contacts or terminals (not depicted). For binary embodiments, each set of terminals may include a line-in terminal and line-to-load terminal, and may be in one of two states. These states include 'open' and 'closed,' and correspond to the actuator 220 having a state of 'off' or 'on,' respectively. In the open-state, the terminals are disconnected such that electricity cannot flow between the terminals. Conversely, the terminals are connected such that electricity can flow between the terminals in the closed-state.

In certain facility systems, actuator 220 may further include a dimmer switch (in lighting systems) or other type of variable voltage device by which variable power may be supplied to the electrical load device 210 based on a setting of the actuator 220. Accordingly, intermediate states between on and off may be controlled by actuator 220. For example, such state could be '40% power,' where off-state and on-state correspond to '0% power' and '100% power,' respectively. Although dimmer switches are generally associated with lighting fixtures, other variable voltage devices may be associated with other electricity consuming appliances having multiple operational settings such as fans.

Actuator 220 may control electrical load device (also known as electrical load) 210 by regulating the amount of power provided to electrical load device 210 from power source 240. The control of electric load 210 in sensor system 200 is based on whether or not power source 240 supplies power to electrical load device 210 via actuator 220. Further, the degree of control may be limited to turning on the device associated the load (i.e., power is supplied) and turning off the device (i.e., power is not supplied).

Since the power supply is controlled by actuator 220 in prior art sensor system 200, a relay failure may disrupt the power supply from power source 240 to electrical load 210. Further, where control of electric load 210 is based on information received by actuator 220 from sensor 230, a break in communication between actuator 220 and sensor 230 may disrupt the control of electric load 210.

Power source 240 may be any power source known in the art and may take on several forms in accordance with various embodiments. For example, power source 240 may be a battery (e.g., lithium, alkaline) to provide power to electrical load device 210. In other embodiments, power source 240 may be a capacitor capable of storing energy for a specified time span (e.g., several days). A current transformer, AC/DC power converter, or other means of obtaining power may be used to charge the battery or capacitor to supply power to the electrical load device 210. Power source 240 may alternatively be a photovoltaic cell (not shown) configured to harvest light energy or charge a battery or capacitor included in power source 240. Power source 240 may further encompass any type of device used to process and/or carry energy to electrical load device 210.

Figure 3:
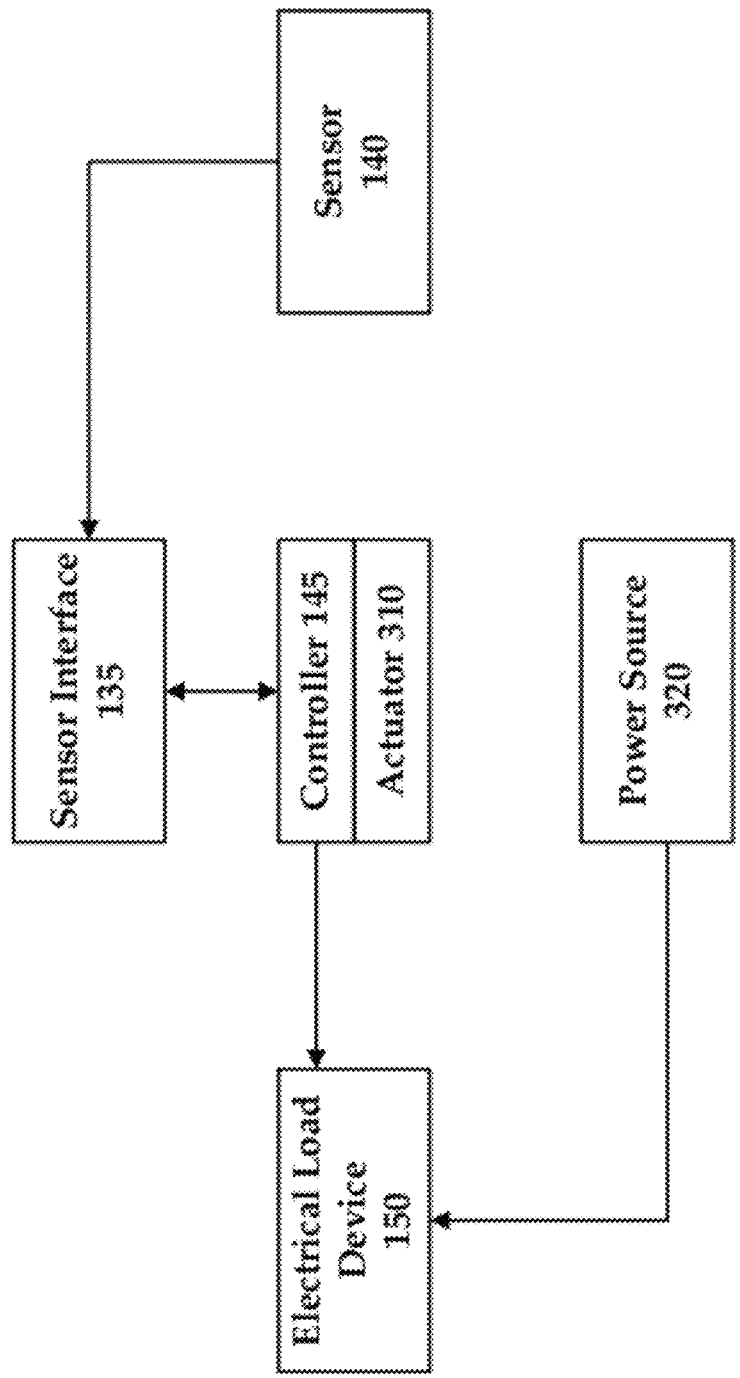
FIG. 3 is a diagram of a system for enabling wireless communication with a wired sensor according to an exemplary embodiment of the present invention.

FIG. 3 is a diagram of a system 300 for enabling wireless communication with a wired sensor according to an exemplary embodiment of the present invention. System 300 includes sensor interface 135, sensor 140, controller 145, electrical load device 150, actuator 310, and power source 320. The controller 145 may therefore be directly connected to the electrical load device 150, while power may be supplied continuously from power source 320 rather than being supplied under control by the actuator 310. Breaking connection between the actuator 310 and the electrical load device 150 allows for independence from any relay or relay failure. In contrast to the system 200 illustrated in FIG. 2, FIG. 3 illustrates that communication between the sensor 140 and actuator 310 may also be disrupted. Disrupting the connection between the sensor 140 and actuator 310 may allow for control of very large electrical loads.

As illustrated in FIG. 3, sensor interface 135 may be coupled to sensor 140 and, further, be in communication with controller 145. Sensor interface 135 may receive a signal indicating a detected environmental condition from sensor 140 and wirelessly transmit that information, with or without additional analysis, to controller 145. Sensor interface 135 may also manage, monitor, and/or track information regarding the sensor 140. For example, sensor interface 135 may track the conditions detected by sensor 140 over time, evaluate the information regarding the detected conditions, monitor when sensor 140 is the most or least active, etc. Such data may be stored locally in a memory associated with the sensor interface 135 or controller 145. Alternatively or in addition, such data may also be sent to database 125 or administrator station 130.

Sensor interface 135 allows for adjustment of a sensor response or sensor setting without having to reprogram the sensor 140 itself. For example, a sensor may be programmed to send a signal to controller 145 in a particular office after ten minutes in which no movement is detected. Adjusting the time delay generally requires that sensor 140 be adjusted manually. The sensor interface 135 allows, however, for the time delay may be adjusted via wireless transmission of instructions. In some instances, the instructions may further allow for intelligent determinations based on specified conditions. For example, the time delay may be set to be shorter on nights, weekends, holidays, etc., than during working hours. As such, lights would be less prone to turning off during peak working hours. The time delay may also correspond to daylight levels, for example, as determined by a light sensor 140 in the room or elsewhere in the facility. Administrator station 130 may be used to program or adjust the operation or settings of sensor 140 via instructions wirelessly transmitted to sensor interface 135.

Controller 145 and actuator 310 may be separate, but associated, devices, as illustrated in FIG. 3. In some cases, however, controller 145 and actuator 310 may also be integrated in one device. Whereas in prior art systems such as that system 200 illustrated in FIG. 2, the actuator 220 may exert control over the operation of electrical load device 210 by intervening in the power supplied by power source 240, thereby turning electrical load device 210 on by supplying power and turning electrical load device 210 off by cutting off power. In contrast, system 300 illustrated in FIG. 3 allows for power to be supplied continuously from power source 320 to electrical load device 150. Further, operation of the electrical load device 150 is directly controlled by controller 145. As such, to effect a change in the operation of electrical load device 150, the other components of system 300 (e.g., sensor 140 via sensor interface 135, actuator 310) send information over a wired or wireless connection to controller 145.

Providing for wireless control allows for more sophisticated controls than were previously possible. For example, the controller 145 may control multiple relays, each exercising individual control over electrical load device (e.g., a lamp in a lighting device with multiple lamps). As such, the controller 145 may individually turn on one, two, three or more lamps in the lighting device. Such individual control allows for stepped lighting levels, which can serve to produce the same result as a dimmer without requiring installation of a dimmer. Providing for stepped lighting levels further allows for conservation of energy in situations where activation of all lights is unnecessary. Presently available systems for stepped lighting (e.g., lacking wireless control) usually involves multiple wall switches, each switch being associated with a different set of lights. Wireless control allows for such stepped lighting without rewiring existing installations of light.

Further, in situations where an occupancy sensor indicates that a room may not be occupied, the ability to provide stepped lighting allows for a more gradual transition from full light to no light. In addition to responding to sensor signals, stepped lighting may be initiated based on a signal from a switch, web control, a remote control device, demand response, or any combination of the foregoing. Demand response may involve receipt and response to signals from a utility company or other party, which allows for "rolling dimming" as an alternative to "rolling blackouts."

Figure 4:
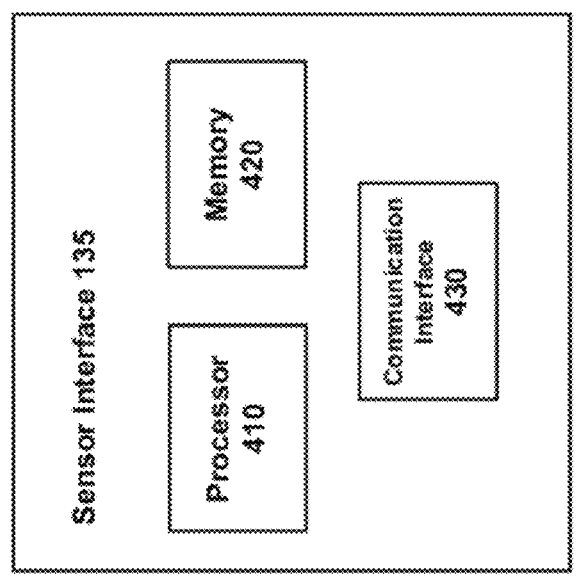
FIG. 4 is a block diagram of the sensor interface of FIG. 3.

FIG. 4 is a block diagram 400 of the sensor interface of FIG. 3. FIG. 4 includes processor 410, memory 420, and communication interface 430. Processor 410 may comprise a microcontroller, a microprocessor, or an application-specific integrated circuit (ASIC), or any other type of processor known in the art. Processor 410 may execute programs stored in memory 420. Depending on the information received from sensor 140, processor 410 may detect the presence and determine the type of sensor 140 in communication network 110. Processor 410 may analyze information about various environmental conditions or factors detected by sensor 140 (e.g., past/present occupancy, past/present energy usage) to verify that sensor 140 is functioning properly.

Sensor interface 135 may further include memory 420 for storing information received from sensor 140. Such information may include data about environmental conditions and other data from other sources, including time of day, occupancy information, schedules, current lighting levels, natural light levels, signals from a centralized control system, automated signals from a utility company or other entity (e.g., demand response), previously designated energy usage preferences, or past or typical energy usage, etc.

Sensor interface 135 may include a communication interface 430 (e.g., a transceiver) for transmitting information using wireless radio frequency (RF) communication. The communication interface 430 may comprise virtually any device known in the art for converting data at a physical data rate and for generating and/or receiving a corresponding RF signal. The communication interface 430 may include, for example, a radio modulator/demodulator for converting data received by sensor interface 135 (e.g., from sensor 140) into the RF signal for transmission to controller 145. The communication interface 430 may also comprise circuitry for receiving data packets and circuitry for converting the data packets into 802.11 compliant RF signals. Various other hardware and/or software devices and/or elements may be integrated with communication interface 430 (e.g., physical integration or a communicative coupling) as to allow for the processing and/or conversion of various other data formats into 802.11 compliant RF signals. In some embodiments, the communication interface 430 may include a radio transmitter or antenna to transmit signals to controller 145. In one embodiment, sensor interface 135 incorporates wireless RF technology such as the ZigBee® standard.

Using communication interface 430, sensor interface 135 may receive information indicative of a detected environmental condition from sensor 140. Communication interface 430 may also generate and wirelessly transmit a signal indicative of a detected environmental condition to controller 145. The controller 145 may then control electrical load device 150 based on the signal. For example, if sensor interface 135 receives information from sensor 140 that senses or detects that a lighting fixture switch has changed (e.g., from 'off' to 'on'), communication interface 430 may generate and wirelessly transmit a signal to controller 145 to indicate the change in condition. Accordingly, controller 145 may turn the electrical load device 150 on.

Figure 5:
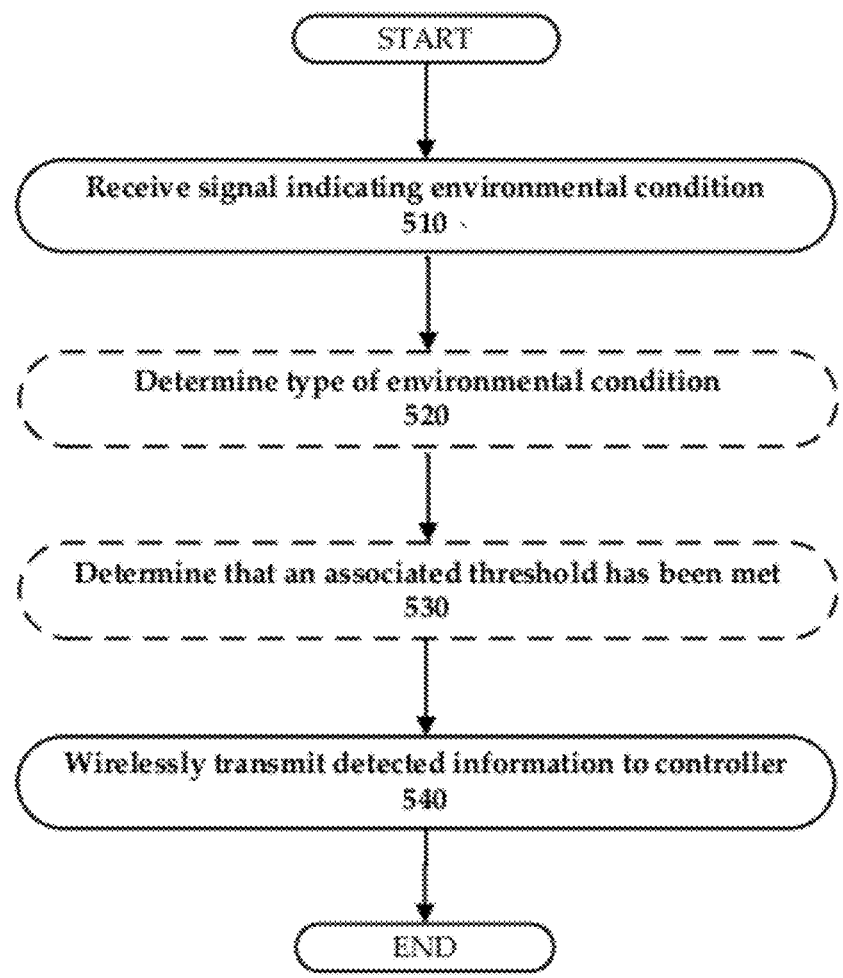
FIG. 5 is a flowchart illustrating an exemplary method for enabling wireless communication with a wired sensor.

FIG. 5 is a flowchart illustrating an exemplary method 500 for enabling wireless communication with a wired sensor. The steps identified in FIG. 5 (and the order thereof) are exemplary and may include various alternatives, equivalents, or derivations thereof including but not limited to the order of execution of the same. The steps of the method of FIG. 5 (and its various alternatives) may be embodied in hardware or software including a computer-readable storage medium (e.g., optical disc, memory card, etc.) comprising instructions executable by a processor of a computing device.

In the method 500, a signal indicating a detected environmental condition is received. A type of the environmental condition may be determined. Further, a threshold associated with the type of environmental condition may be determined to have been met. Based on the threshold having been met, information regarding the detected environmental condition may be wirelessly transmitted to a controller 145.

In step 510, a signal indicating a detected environmental condition is sent from wired sensor 140 and received by sensor interface 135. As discussed herein, sensor 140 may be any type of sensor known in the art such as an occupancy or light sensor. In some instances, a sensor 140 may encompass multiple, different sensors, thereby being capable of detecting multiple types of conditions. For example, a sensor 140 may detect both light and occupancy.

In instances where a wired sensor is only capable of detecting one type of environmental condition, the type of sensor and the environmental condition it detects may have been previously identified or provided to sensor interface 135. Alternatively, in step 520, sensor interface 135 may determine the type of the environmental condition detected by sensor 140, as indicated by the signal sent in step 510. The received signal may be evaluated to determine whether it has characteristic features of a certain environmental condition (e.g., voltage pattern, range of voltage). Occupancy sensors may be associated with a stepped voltage pattern, whereas a light sensor may detect varying levels of light associated with a more gradual pattern that may coincide with daylight hours.

In step 530, it is determined that a threshold associated with the type of environmental condition has been met. To manage the sensitivity of the sensor 140 and responses to the particular conditions detected by the sensor 140, a threshold may be set at the sensor interface 135. For example, a threshold associated with occupancy may require that occupancy be detected for a predetermined number of seconds. Likewise, a threshold associated with light levels may require that predetermined light levels be reached before activating or deactivating any lamps. Such thresholds may also be based on other parameters, such as schedules, so that the threshold may increase or decrease based on the day of the week.

In step 540, sensor interface 135 wirelessly transmits information concerning the environmental condition detected by sensor 140 to controller 145, which may control the operation of electrical load device 150 based on the detected information wirelessly transmitted from sensor interface 135. In response to detection of movement or lack thereof, for example, controller 145 may direct electrical load device 150 to turn on, turn off, or adjust dimming of a lighting fixture (or a selective portion thereof).

Figure 6:
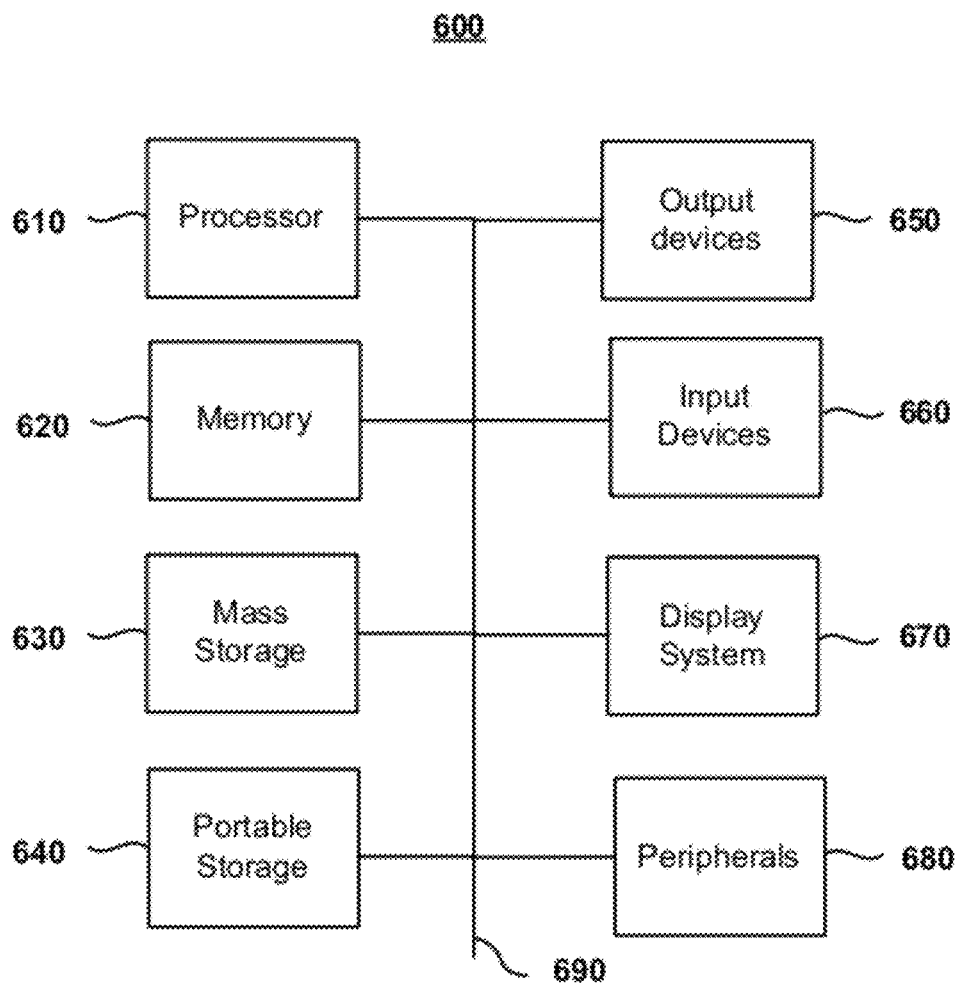
FIG. 6 illustrates an exemplary computing system that may be used to implement an embodiment of the present invention.

FIG. 6 illustrates an exemplary computing system 600 that may be used to implement an embodiment of the present invention. Computing system 600 of FIG. 6 may be implemented, for example, in the context of administrator station 130 (illustrated in FIG. 1). The computing system 600 of FIG. 6 includes one or more processors 610 and main memory 620. Main memory 620 stores, in part, instructions and data for execution by processor 610. Main memory 620 may store the executable code when in operation. Main memory 620 may also include database 125 (see FIG. 1). The database in main memory 620 may also store information about environmental factors and other data such as the time of day, occupancy information, schedules, current lighting levels, natural light levels, signals from a centralized control system, automated signals from a utility company or other entity (e.g., demand response), previously designated energy usage preferences, or past or typical energy usage, etc.

The computing system 600 of FIG. 6 further includes a mass storage device 630, portable storage device(s) 640, output devices 650, user input devices 660, a display system 670, and peripherals 680. The components shown in FIG. 6 are depicted as being connected via a single bus 690. The components, however, may be connected through one or more data transport means. For example, processor 610 and main memory 620 may be connected via a local microprocessor bus, and mass storage device 630, peripherals 680, portable storage device 640, and display system 670 may be connected via one or more input/output (I/O) buses.

Mass storage device 630, which may be implemented with a magnetic disk drive or an optical disk drive, is a non-volatile storage device for storing data and instructions for use by processor 610. Mass storage device 630 may store the system software for implementing embodiments of the present invention for purposes of loading software into main memory 620.

Portable storage device 640 operates in conjunction with a portable non-volatile storage medium, such as a floppy disk, compact disk or Digital video disc, to input and output data and code to and from the computing system 600 of FIG. 6. The system software for implementing embodiments of the present invention may be stored on such a portable medium and input to the computing system 600 via the portable storage device 640.

Input devices 660 provide a portion of a user interface. Input devices 660 may include an alpha-numeric keypad, such as a keyboard, for inputting alpha-numeric and other information, or a pointing device, such as a mouse, a trackball, stylus, or cursor direction keys. Additionally, the computing_system 600 as shown in FIG. 6 includes output devices 650. Examples of suitable output devices include speakers, printers, network interfaces, and monitors.

Display system 670 may include a liquid crystal display (LCD) or other suitable display device. Display system 670 receives textual and graphical information, and processes the information for output to the display device.

Peripherals 680 may include any type of computer support device to add additional functionality to the computer system. For example, peripherals 680 may include a modem or a router.

The components contained in the computing system 600 of FIG. 6 are those typically found in computer systems that may be suitable for use with embodiments of the present invention and are intended to represent a broad category of computer components that are well known in the art. Thus, computing system 600 of FIG. 6 may be a personal computer, hand held computing device, telephone, mobile computing device, workstation, server, minicomputer, mainframe computer, or any other computing device. The computer may also include different bus configurations, networked platforms, multi-processor platforms, etc. Various operating systems may be used including Unix, Linux, Windows, Macintosh OS, Palm OS, and other suitable operating systems.

The terms "computer-readable storage medium" and "computer-readable storage media" as used herein refer to a medium or media that participates in providing instructions to a CPU for execution. Such media may take many forms including, but not limited to, non-volatile and volatile media. Non-volatile media include, for example, optical or magnetic disks, such as a fixed disk. Volatile media include dynamic memory, such as system RAM. Common forms of computer-readable storage media include, for example, a floppy disk, a flexible disk, a hard disk, magnetic tape, any other magnetic medium, a CD-ROM disk, digital video disk (DVD), any other optical medium, punch cards, paper tape, any other physical medium with patterns of marks or holes, a RAM, a PROM, an EPROM, a FLASHEPROM, any other memory chip or cartridge.

While various embodiments have been described above, it should be understood that they have been presented by way of example only, and not limitation. The descriptions are not intended to limit the scope of the invention to the particular forms set forth herein. Thus, the breadth and scope of a preferred embodiment should not be limited by any of the above-described exemplary embodiments.

To the contrary, the present descriptions are intended to cover such alternatives, modifications, and equivalents as may be included within the spirit and scope of the invention as defined by the appended claims and otherwise appreciated by one of ordinary skill in the art. The scope of the invention should, therefore, be determined not with reference to the above description, but instead should be determined with reference to the appended claims along with their full scope of equivalents.

What is claimed is:

1. A system for enabling wireless communication with a wired sensor, the system comprising:
   a power source for supplying continuous power to an electrical load device, operation of the electrical load device controlled by a controller; and
   a sensor interface communicatively coupled to the wired sensor, wherein the sensor interface:
      receives information indicating a plurality of environmental conditions detected by the wired sensor, and
      wirelessly transmits the information regarding the detected plurality of enviornmental conditions received from the wired sensor to the controller, wherein the controller controls operation of the electrical load device based on the information wirelessly transmitted from the sensor interface.

2. The system of claim 1, further comprising a memory for storing preferences set by an administrator, the preferences concerning operational parameters of the wired sensor.

3. The system of claim 1, wherein the sensor interface is further configured to determine at least one type of environmental condition detected by the wired sensor.

4. The system of claim 3, wherein the sensor interface is further configured to analyze the received information based on the determined type.

5. The system of claim 1, wherein the sensor interface is further configured to set a threshold associated with the detected plurality of environmental conditions and wherein the information is wirelessly transmitted to the controller when the threshold is met.

6. The system of claim 5, wherein the sensor interface is further configured to receive updates wirelessly sent from an administrator and wherein the threshold is updated based on the received updates.

7. The system of claim 5, wherein the threshold is further based on specified parameters concerning conditions other than the detected plurality of environmental conditions.

8. The system of claim 1, wherein the electrical load device is a lighting fixture and controlling the electrical load device includes providing stepped lighting levels by individually activating one or more lights of a plurality of lights in the lighting fixture.

9. A method for enabling wireless communication with a wired sensor, the method comprising:
   monitoring the wired sensor for generation of a signal indicating detection of a plurality environmental conditions;
   receiving the signal from the wired sensor at a sensor interface, the signal including information regarding the plurality of environmental conditions detected by the wired sensor; and
   wirelessly transmitting the information regarding the detected plurality of environmental conditions from the sensor interface to a wireless controller, wherein the wireless controller controls operation of an electrical load device based on the information wirelessly transmitted from the sensor interface.

10. The method of claim 9, further comprising storing preferences in a memory associated with the sensor interface, the preferences concerning operational parameters of the wired sensor.

11. The method of claim 9, further comprising determining at least one type of environmental condition detected by the wired sensor.

12. The method of claim 11, further comprising analyzing the received information based on the determined type.

13. The method of claim 9, further comprising setting a threshold associated with the detected plurality of environmental conditions, wherein the information is wirelessly transmitted to the wireless controller when the threshold is met.

14. The method of claim 13, further comprising receiving updates wirelessly sent from an administrator and updating the threshold based on the received updates.

15. The method of claim 13, wherein the threshold is further based on specified parameters concerning conditions other than the detected plurality of environmental conditions.

16. The method of claim 9, wherein the electrical load device is a lighting fixture, wherein the signal wirelessly transmitted to the wireless controller indicates a detected lighting level, and wherein responsive control of the electrical load device includes providing stepped lighting levels by individually activating or deactivating one or more lights of a plurality of lights in the lighting fixture.

17. An apparatus for enabling wireless communication with a wired sensor located within a network, the apparatus comprising:
   a communication interface for:
      receiving a signal from the wired sensor determined to be present in the network, the signal including information regarding a plurality of environmental conditions detected by the wired sensor;
      wirelessly transmitting the information regarding the detected plurality environmental conditions to a controller for controlling an electrical load device based on the information; and
   a memory to store information detected by the wired sensor.

18. The apparatus of claim 17, further comprising a processor for executing instructions stored in memory, wherein execution of the instructions by the processor:

determines at least one type of environmental condition detected by the wired sensor; and analyzes the received information based on the determined type, wherein analysis includes setting a threshold associated with the determined type of the detected plurality of environmental conditions, wherein the information is wirelessly transmitted to the controller when the threshold is met.

19. The apparatus of claim 18, wherein the communication interface receives updates wirelessly sent from an administrator and wherein the threshold is updated based on the received updates.

20. A non-transitory computer-readable storage medium having embodied thereon a program, the program being executable by a processor to perform a method for enabling wireless communication with a wired sensor, the method comprising:

receiving a signal from the wired sensor, the signal indicating detection of a plurality of environmental conditions by the wired sensor;

determining a type of the plurality of environmental conditions detected by the wired sensor;

determining that a threshold associated with the determined type of the plurality of environmental conditions has been met; and wirelessly transmitting information regarding the detected plurality of environmental conditions from the wired sensor to a wireless controller, wherein the wireless controller controls operation of an electrical load device based on the information wirelessly transmitted from the wireless sensor.

* * * * *